United States Patent [19]

Tachibana

[11] Patent Number: 5,182,396
[45] Date of Patent: Jan. 26, 1993

[54] 1-HYDROXYVITAMIN D DERIVATIVES

[75] Inventor: Yoji Tachibana, Kawagoe, Japan

[73] Assignee: Nisshin Flour Milling Co., Ltd., Tokyo, Japan

[21] Appl. No.: 857,373

[22] Filed: Mar. 25, 1992

[30] Foreign Application Priority Data

Mar. 29, 1991 [JP] Japan .................................. 3-89175

[51] Int. Cl.⁵ ............................................ C07J 175/00
[52] U.S. Cl. ................................................... 552/653
[58] Field of Search ......................................... 552/653

[56] References Cited

PUBLICATIONS

Paaren et al., *J. of Org. Chem.*, 45, pp. 3253-3258 (1980).

*Primary Examiner*—Marianne M. Cintins
*Assistant Examiner*—Kimberly J. Kestler
*Attorney, Agent, or Firm*—Abelman Frayne & Schwab

[57] ABSTRACT

1-Hydroxyvitamin D derivatives which are esters of 1-hydroxyvitamin D with vitamin A acid. They are useful for an agent for preventing and treating osteoporosis, cutaneous ulcer and tumor.

7 Claims, No Drawings

1-HYDROXYVITAMIN D DERIVATIVES

BACKGROUND OF THE INVENTION

1. Field of the Invention

This invention relates to novel 1-hydroxyvitamin D derivatives.

More particularly, it is concerned with esters of 1-hydroxyvitamin D with vitamin A acid.

The 1-hydroxyvitamin D derivatives are useful as an agent for preventing or treating osteoporosis, cutaneous ulcers and tumors.

2. Description of the Prior Art

There have been widely used active vitamin D having a hydroxyl group at the 1-position of the vitamin D as an agent for treating osteoporosis. Recently, the vitamin D derivatives have been found to have inducing activities on the differentiation of cells and tried to apply to the treatment of psoriasis and tumors.

On the other hand, vitamin A acid is biochemically synthesized from vitamin A and guessed to be an active intermediate at the expression of vitamin A effects. It is clarified that the functions of vitamin A such as growth stimulation, protein metabolism and stabilization of cuticula cell tissues are achieved via vitamin A acid. Considering those activities of vitamin A acid, there has been an idea to get useful compounds by esterification of such vitamin A acid with alcohols having physiological activities. For example, Japanese patent unexamined publication Nos. 469/1973 and 92967/1979 disclose esters of vitamin A acid with α-tocopherol (vitamin E). However, none of esters of vitamin A acid with vitamin D is known.

SUMMARY OF THE INVENTION

It is an object of the invention to provide 1-hydroxyvitamin D derivatives which are useful as an agent for preventing or treating osteoporosis, cutaneous ulcers and tumors.

DETAILED DESCRIPTION OF THE INVENTION

In accordance with the invention there are provided novel 1-hydroxyvitamin D derivatives having the formula (I)

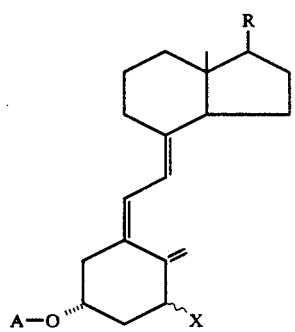

wherein A represents an acyl residue derived from vitamin A acid, X means a hydroxyl group and R represents a group of the formula (II)

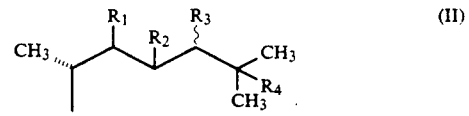

wherein $R_1$ and $R_2$ each represent hydrogen atoms or together form a carbon-carbon double bond, $R_3$ represents a hydrogen atom, a $C_1$-$C_4$ alkyl group or a hydroxyl group and $R_4$ represents a hydrogen atom or a hydroxyl group.

In the above formula (I), A represents an acyl group derived from vitamin A acid. The acyl group may be one derived from all trans-vitamin A acid having the formula (III)

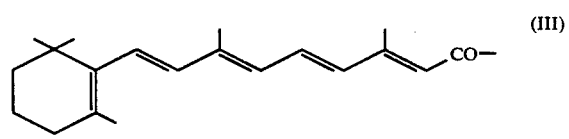

or one derived from 13-cis-vitamin A acid having the formula (IV)

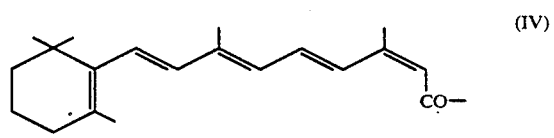

X represents a hydroxyl group. $R_1$ and $R_2$ each represent hydrogen atoms or together form a carbon-carbon double bond.

$R_3$ represents a hydrogen atom, $C_1$-$C_4$ alkyl group or a hydroxyl group. The alkyl group may be straight or branched and include, for example, methyl, ethyl, n-propyl, isopropyl, n-butyl and isobutyl $R_4$ represents a hydrogen atom or a hydroxyl group.

In the above formula (I), X can be bonded to the asymmetric carbon atom to form α- or β-configuration.

In case where $R_3$ is a $C_1$-$C_4$ alkyl group or a hydroxyl group, it can be bonded to the asymmetric carbon atom to form R- or S-configuration.

In case where $R_1$ and $R_2$ together form the carbon-carbon double bond, it can be trans or cis form.

The 1-hydroxyvitamin D derivatives (I) can be prepared by protecting hydroxyl groups existing in 3β-acetoxy-1-hydroxyvitamin D (V) to give the compound (VI), deacetylating the latter compound to afford the compound (VII), subjecting the latter compound to esterification with vitamin A acid to obtain the compound (VIII) and then eliminating the hydroxyl-protecting group in the compound (VIII). The above process can be illustrated by the following reaction sequence:

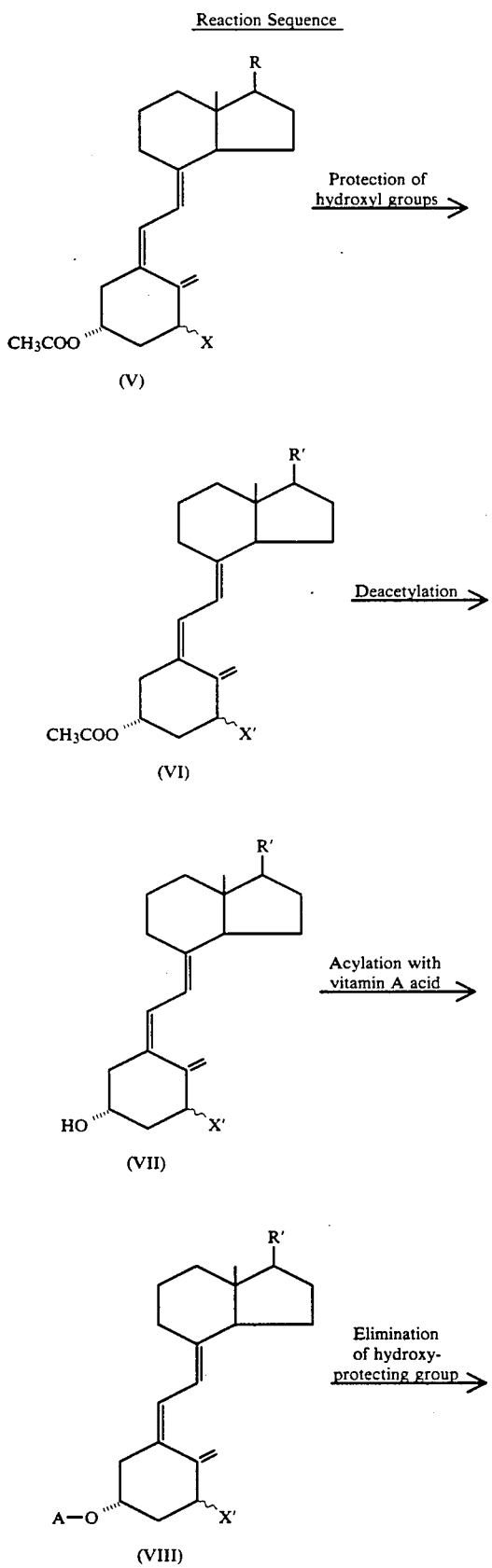

-continued
Reaction Sequence

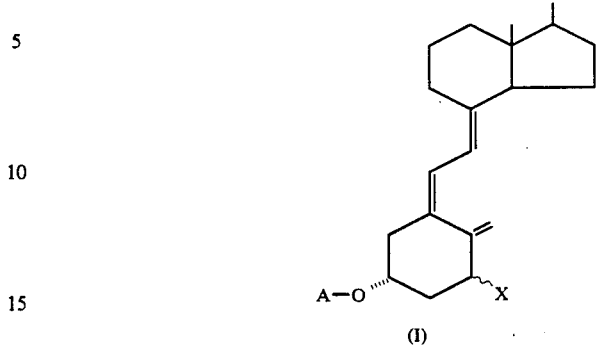

In the above formulae, A, X and R have the same meanings as defined above, X' represents a protected hydroxyl group and R' represents a group of the formula (IX)

$$CH_3 \overset{R_1}{\underset{}{\cdots}} \overset{R_2}{\underset{}{\cdot}} \overset{R_3'}{\underset{CH_3}{\cdot}} \overset{CH_3}{\underset{R_4'}{\cdot}} \quad (IX)$$

In the above formula (IX), $R_1$ and $R_2$ have the same meanings as defined above, $R'_3$ represents a hydrogen atom, a $C_1-C_4$ alkyl group or a protected hydroxyl group and $R'_4$ represents a hydrogen atom or a protected hydroxyl group.

The hydroxyl-protecting groups in $R'_3$ and $R'_4$ are desirably such groups that can chemically be distinguished from the acetyl group of the 3-position and can easily be eliminated without decomposing the forms of vitamin A and vitamin D. Preferable examples of such groups include a t-butyldimethylsilyl group or a triethylsilyl group. The above compound (V) is a known compound disclosed in Deluca, J. Org. Chem. 45, 3253 (1980).

The compound (VI) can be prepared by protecting the free hydroxyl groups existing in the compound (V) by a conventional means. For example, the compound (VI) can be obtained by reacting the compound (V) with t-butyldimethylsilyl chloride or triethylsilyl chloride in the presence of a weak base such as imidazole in an inert organic solvent such as dimethylformamide.

The compound (VII) can be prepared by selectively eliminating the 3-acetyl group of the compound (VI) by a conventional means. For instance, the compound (VII) can be obtained by treating the compound (VI) with an alkali such as sodium or potassium hydroxide in a lower alcohol such as methanol and ethanol.

The compound (VIII) can be prepared by reacting the compound (VII) with vitamin A acid or its reactive derivatives by a conventional means. For instance, the compound (VIII) can be obtained by reacting the compound (VII) with vitamin A acid in the presence of a dehydrating agent such as dicyclohexylcarbodiimide or trifluoroacetic anhydride in an inert organic solvent such as isopropyl ether and tetrahydrofuran. Alternatively, it can be obtained by reacting the compound (VII) with a reactive derivative of vitamin A, for example, the acid halide or the acid anhydride. It is desirable to carry out the reaction in mild reaction conditions in order to retain the geometrical isomerism of the double bond of vitamin A acid and to prevent isomerization and ring closure. In view of the point, there can preferably be used trifluoroacetic anhydride.

The compound (I) can be obtained by eliminating the hydroxy-protecting groups in the compound (VIII) by a conventional means. For example, it can be prepared by treating the compound (VIII) with a weak base such as tetrabutylammonium fluoride in an inert organic solvent, e.g., tetrahydrofuran.

The product obtained in each of the above reactions can be purified by a conventional means. For instance, a solvent used in the reaction is distilled off from the reaction mixture and the resulting residue is purified by recrystallization or chromatography. Alternatively, the reaction mixture is extracted with a proper organic solvent and the solvent is distilled off from the extract and the resulting residue is purified by recrystallization or chromatography.

The compound (VIII) obtained by the acylation of the compound (VII) with vitamin A acid is desirably used in the next eliminating step without purification.

Examples of the compounds (I) and its intermediates (V)–(VIII) are listed in the following Tables 1–5. The compound numbers in the tables are referred to in Examples below.

"Double bond" appearing in Tables 1–5 represents that $R_1$ and $R_2$ together form trans-double bond.

In Tables 3–5, Z represents a t-butyldimethylsilyl group and Z' represents a triethylsilyl group.

TABLE 1

The compounds (I)

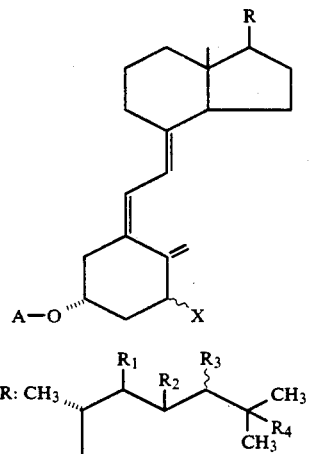

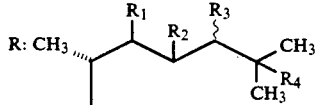

| Compound No. | A | X | $R_1$ | $R_2$ | $R_3$ | $R_4$ |
|---|---|---|---|---|---|---|
| I-1 | Acyl group (III) (all-trans) | α-OH | H | H | H | H |
| I-2 | Acyl group (III) (all-trans) | β-OH | " | " | " | " |
| I-3 | Acyl group (III) (all-trans) | α-OH | double bond | CH$_3$(R) | H | |
| I-4 | Acyl group (III) (all-trans) | β-OH | " | " | " | |
| I-5 | Acyl group (III) (all-trans) | α-OH | H | H | H | OH |
| I-6 | Acyl group (III) (all-trans) | β-OH | " | " | " | " |
| I-7 | Acyl group (III) | α-OH | double bond | CH$_3$(S) | OH | |
| I-8 | Acyl group (III) (all-trans) | β-OH | " | " | " | |
| I-9 | Acyl group (III) (all-trans) | α-OH | H | H | OH(R) | H |
| I-10 | Acyl group (III) (all-trans) | α-OH | H | H | OH(S) | OH |
| I-11 | Acyl group (IV) (13-cis) | α-OH | H | H | H | H |
| I-12 | Acyl group (IV) (13-cis) | β-OH | " | " | " | " |
| I-13 | Acyl group (IV) (13-cis) | α-OH | double bond | CH$_3$(R) | H | |
| I-14 | Acyl group (IV) (13-cis) | β-OH | " | " | " | |
| I-15 | Acyl group (IV) (13-cis) | α-OH | H | H | H | OH |
| I-16 | Acyl group (IV) (13-cis) | β-OH | " | " | " | " |
| I-17 | Acyl group (IV) (13-cis) | α-OH | double bond | CH$_3$(S) | OH | |
| I-18 | Acyl group (IV) (13-cis) | β-OH | " | " | " | |

TABLE 2

The compounds (V)

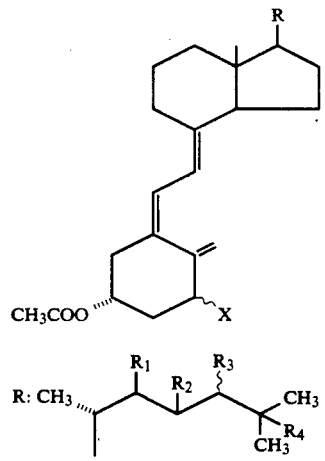

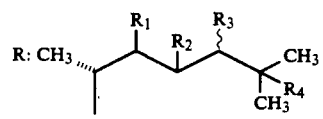

| Compound No. | X | $R_1$ | $R_2$ | $R_3$ | $R_4$ |
|---|---|---|---|---|---|
| V-1 | α-OH | H | H | H | H |
| V-2 | β-OH | " | " | " | " |
| V-3 | α-OH | double bond | CH$_3$(R) | H | |
| V-4 | β-OH | " | " | " | |
| V-5 | α-OH | H | H | H | OH |
| V-6 | β-OH | " | " | " | " |
| V-7 | α-OH | double bond | CH$_3$(S) | OH | |
| V-8 | β-OH | " | " | " | |
| V-9 | α-OH | H | H | OH(R) | H |
| V-10 | α-OH | H | H | OH(S) | OH |

TABLE 3

The compounds (VI)

TABLE 3-continued

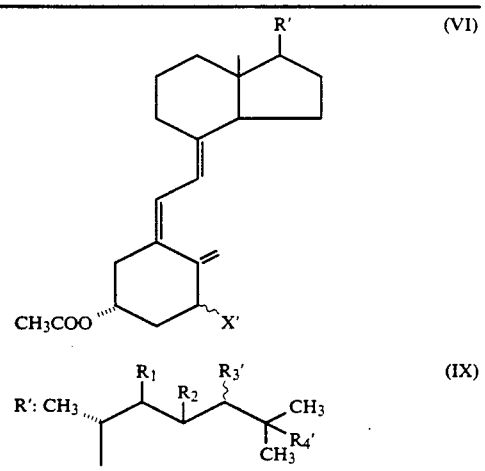

| Compound No. | X' | R₁ | R₂ | R₃' | R₄' |
|---|---|---|---|---|---|
| VI-1 | α-OZ | H | H | H | H |
| VI-2 | β-OZ | " | " | " | " |
| VI-3 | α-OZ | double bond | | CH₃(R) | H |
| VI-4 | β-OZ | " | | " | " |
| VI-5 | α-OZ' | H | H | H | OZ' |
| VI-6 | β-OZ' | " | " | " | " |
| VI-7 | α-OZ' | double bond | | CH₃(S) | OZ' |
| VI-8 | β-OZ' | " | | " | " |
| VI-9 | α-OZ' | H | H | OZ'(R) | H |
| VI-10 | α-OZ' | H | H | OZ'(S) | OZ' |

TABLE 4

The compounds (VII)

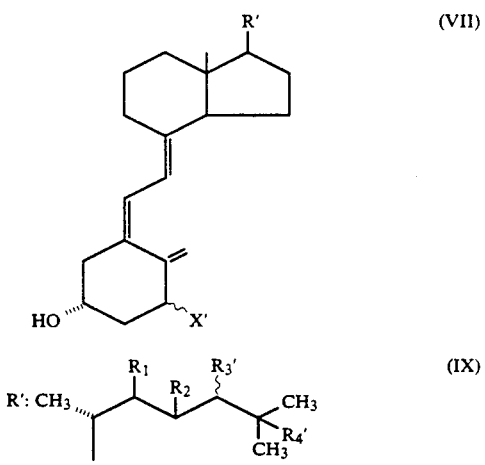

| Compound No. | X' | R₁ | R₂ | R₃' | R₄' |
|---|---|---|---|---|---|
| VII-1 | α-OZ | H | H | H | H |
| VII-2 | β-OZ | " | " | " | " |
| VII-3 | α-OZ | double bond | | CH₃(R) | H |
| VII-4 | β-OZ | " | | " | " |
| VII-5 | α-OZ' | H | H | H | OZ' |
| VII-6 | β-OZ' | " | " | " | " |
| VII-7 | α-OZ' | double bond | | CH₃(S) | OZ' |
| VII-8 | β-OZ' | " | | " | " |
| VII-9 | α-OZ' | H | H | OZ'(R) | H |
| VII-10 | α-OZ' | H | H | OZ'(S) | OZ' |

TABLE 5

The compounds (VIII)

TABLE 5-continued

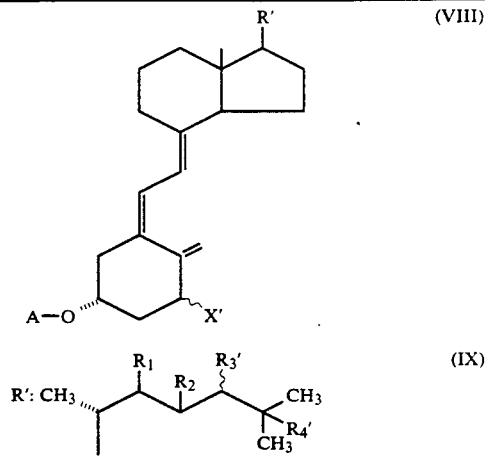

| Compound No. | A | X' | R₁ | R₂ | R₃' | R₄' |
|---|---|---|---|---|---|---|
| VIII-1 | Acyl group (III) (all-trans) | α-OZ | H | H | H | H |
| VIII-2 | Acyl group (III) (all-trans) | β-OZ | " | " | " | " |
| VIII-3 | Acyl group (III) (all-trans) | α-OZ | double bond | | CH₃(R) | H |
| VIII-4 | Acyl group (III) (all-trans) | β-OZ | " | | " | " |
| VIII-5 | Acyl group (III) (all-trans) | α-OZ' | H | H | H | OZ' |
| VIII-6 | Acyl group (III) (all-trans) | β-OZ' | " | " | " | " |
| VIII-7 | Acyl group (III) (all-trans) | α-OZ' | double bond | | CH₃(S) | OZ' |
| VIII-8 | Acyl group (III) (all-trans) | β-OZ' | " | | " | " |
| VIII-9 | Acyl group (III) (all-trans) | α-OZ' | H | H | OZ'(R) | H |
| VIII-10 | Acyl group (III) (all-trans) | α-OZ' | H | H | OZ'(S) | OZ' |
| VIII-11 | Acyl group (IV) (13-cis) | α-OZ | H | H | H | H |
| VIII-12 | Acyl group (IV) (13-cis) | β-OZ | " | " | " | " |
| VIII-13 | Acyl group (IV) (13-cis) | α-OZ | double bond | | CH₃(R) | H |
| VIII-14 | Acyl group (IV) (13-cis) | β-OZ | " | | " | " |
| VIII-15 | Acyl group (IV) (13-cis) | α-OZ' | H | H | H | OZ' |
| VIII-16 | Acyl group (IV) (13-cis) | β-OZ' | " | " | " | " |
| VIII-17 | Acyl group (IV) (13-cis) | α-OZ' | double bond | | CH₃(S) | OZ' |
| VIII-18 | Acyl group (IV) (13-cis) | β-OZ' | " | | " | " |

The compounds (I) show superior activities on preventing or treating osteoporosis, cutaneous ulcers and tumors.

The 1-hydroxyvitamin D derivatives (I) may be administered orally or parenterally in dosages of from 0.1 μg to 100 μg daily to the human adult in divided doses. The compounds (I) may be compounded and formulated into pharmaceutical preparations in unit dosage form for oral or parenteral administration with organic or inorganic solid materials or liquids which are pharmaceutically acceptable carriers, for example, calcium carbonate, starch, sucrose, lactose, talc, magnesium stearate and the like.

The compounds (I) can be formulated in admixture with pharmaceutcal carriers or excipients by a conventional method into tablets, powders, capsules or granules. In addition to the above-mentioned solid preparations, the compounds (I) may also be formulated into liquid preparations such as injectable oily suspensions or syrups or ointment preparations.

The following examples are intended to illustrate the invention more specifically, but are not to be construed as limiting the scope thereof.

EXAMPLE 1

Preparation of 1α-hydroxycholecalciferol Vitamin A Acid (All-trans Form) Ester (Compound I-1)

(1) Preparation of 3β-acetoxy-1α-t-butyldimethylsilyloxy-vitamin $D_3$ (Compound VI-1)

To a solution of Compound V-1 (600 mg) dissolved in dimethylformamide (5 ml) were added t-butyldimethylsilylchloride (300 mg) and imidazole (300 mg). The mixture was maintained at 40° C. for one hour followed by extraction with ether and washing with brine. The ether was removed by distillation, and the residue was purified by chromatography on silica gel (hexane/ethyl acetate=95/5) to give 620 mg of the title Compound VI-1 (oil).

$^1$H-NMR (CDCl$_3$): δ2.03 (3H, s, COCH$_3$), 4.36 (1H, m, H-1), 4.93 (1H, s, 19-Z), 5.21 (1H, m, H-3), 5.27 (1H, s, 19-E), 6.05, 6.32 (2H, ABq, J=12.0 Hz, H-6, H-7)

(2) Preparation of 1α-t-butyldimethylsilyloxyvitamin $D_3$ (Compound VII-1)

To a solution of Compound VI-1 (500 mg) dissolved in ethanol (5 ml) was added a 10% ethanolic solution of potassium hydroxide (0.5 ml). The mixture was stirred at room temperature for 30 min. followed by extraction with ethyl acetate and washing with brine. The solvent was removed by distillation, and the residue was purified by chromatography on silica gel (hexane/ethyl acetate=9/1) to give 410 mg of the title Compound VII-1 (oil).

$^1$H-NMR (CDCl$_3$): δ4.24 (1H, m, H-3), 4.40 (1H, m, H-1), 4.93 (1H, s, 19-Z), 5.30 (1H, s, 19-E), 6.04, 6.35 (2H, ABq, J=12.1 Hz, H-6, H-7)

(3) Preparation of 1α-hydroxycholecalciferol Vitamin A Acid (All-trans Form) Ester (Compound I-1)

To a mixture of all-trans vitamin A acid (300 mg) and isopropyl ether (3 ml) was dropwise added trifluoroacetic anhydride (0.18 ml). The mixture was stirred for 30 min. To the reaction mixture was dropwise added a tetrahydrofuran solution (5 ml) of Compound VII-1 (400 mg) followed by stirring at room temperature for 2 hours. Addition of aqueous ammonia (0.5 ml), extraction with ether, washing with brine followed by removal of the ether and purification of the residue by chromatography on silica gel (hexane/ethyl acetate=95/5) yielded 490 mg of Compound VIII-1. To a solution of the compound in tetrahydrofuran (5 ml) was added a 1M solution of tetrabutylammonium fluoride (called Bu$_4$NF herein below)(3 ml). Stirring at room temperature for 3 hours followed by extraction with ethyl acetate, washing with brine, removal of the ethyl acetate by distillation and purification of the residue by chromatography on silica gel (hexane/ethyl acetate =9/1) afforded 340 mg of the title Compound I-1.

$^1$-NMR (CDCl$_3$): δ0.55 (3H, s), 0.87 (3H, s), 0.89 (3H, s), 0.93 (3H, d), 1.03 (6H, s), 1.71 (3H, s), 2.01 (3H, s), 2.35 (3H, s), 4.43 (1H, m), 5.00 (1H, s), 5.28 (1H, m), 5.34 (1H, s), 5.74 (1H, s), 6.00–6.36 (6H, m), 7.01 (1H, m)

EXAMPLE 2

Preparation of 1β-hydroxycholecalciferol Vitamin A Acid (All-trans Form) Ester (Compound I-2)

Compound VII-2 was obtained from Compound V-2 via Compound VI-2 in the same procedures as in Example 1(1) and (2).

Compound VII-2 (300 mg) was treated in the same way as in Example 1 to give 220 mg of Compound I-2.

$^1$H-NMR (CDCl$_3$): δ0.55 (3H, s), 0.87 (3H, s), 0.89 (3H, s), 0.93 (3H, d), 1.03 (6H, s), 1.71 (3H, s), 2.01 (3H, s), 2.35 (3H, s), 4.20 (1H, m), 5.00 (1H, m) s), 5.04 (1H, m), 5.36 (1H, s), 5.74 (1H, s), 6.00–6.36 (6H, m), 7.01 (1H, m)

EXAMPLE 3

Preparation of 1-hydroxyergocalciferol Vitamin A Acid (All-trans Form) Ester (Compound I-3)

(1) Preparation of 3β-acetoxy-1α-t-butyldimethylsilyloxy-vitamin $D_2$ (Compound VI-3)

Compound V-3 (400 mg) was treated in the same way as in Example 1(1) to give 410 mg of the title Compound VI-3 (oil).

$^1$H-NMR (CDCl$_3$): δ2.03 (3H, s, COCH$_3$), 4.37 (1H, m, H-1), 4.93 (1H, s, 19-Z), 5.21 (3H, m, H-3, H-22, H-23), 5.29 (1H, s, 19-E), 6.06, 6.31 (2H, ABq, J=12.1 Hz, H-6, H-7)

(2) Preparation of 1α-t-butyldimethylsilyloxyvitamin $D_2$ (Compound VII-3)

Compound VI-3 (300 mg) was treated in the same way as in Example 1(2) to afford 250 mg of the title compound VII-3 (oil).

$^1$H-NMR (CDCl$_3$): δ4.26 (1H, m, H-3), 4.40 (1H, m, H-1), 4.94 (1H, s, 19-Z), 5.23 (2H, m, H-22, H-23), 5.29 (1H, s, 19-E), 6.06, 6.37 (2H, ABq, J=12.1 Hz, H-6, H-7)

(3) Preparation of 1α-hydroxyergocalciferol Vitamin A Acid (All-trans Form) Ester (Compound I-3)

To a mixture of all-trans vitamin A cid (200 mg) and isopropyl ether (2 ml) was added trifluoroacetic anhydride (0.13 ml). The mixture was stirred at room temperature for 15 min. Then a tetrahydrofuran solution (5 ml) of Compound VII-3 (280 mg) was dropwise added, and the mixture was allowed to stand overnight at 5° C. Aqueous ammonia (0.4 ml) was added, and the mixture was stirred for 30 min. and extracted with ether. Washing with brine, subsequent removal of the ether and chromatographing of the residue on silica gel (hexane/ethyl acetate=9/1) afforded 310 mg of Compound VIII-3. To a solution of the compound in tetrahydrofuran (4 ml) was then added a 1M solution of Bu₄NF (2 ml), and the mixture was stirred at room temperature for 4 hours. Extraction with ethyl acetate, washing with brine, removal of the ethyl acetate by distillation and purification of the residue by chromatography on silica gel (hexane/ethyl acetate=9/1) yielded 220 mg of the title Compound I-3.

$^1$H-NMR (CDCl$_3$): δ0.55 (3H, s), 0.82 (3H, d), 0.84 (3H, d), 0.92 (3H, d), 1.01 (3H, d), 1.03 (6H, s), 1.71 (3H, s), 2.00 (3H, s), 2.35 (3H, s), 4.44 (1H, m), 5.01 (1H, s), 5.22 (2H, m), 5.28 (1H, m), 5.34 (1H, s), 5.76 (1H, s), 6.01-6.35 (6H, m), 7.00 (1H, m)

EXAMPLE 4

Preparation of 1β-hydroxyergocalciferol Vitamin A Acid (All-trans Form) Ester (Compound I-4)

Compound VII-4 was prepared from Compound V-4 via Compound VI-4 in the same procedures as in Example 3(1) and (2).

Compound VII-4 (200 mg) was treated in the same way as in Example 3(3) to obtain 150 mg of the title Compound I-4.

$^1$H-NMR (CDCl$_3$): δ0.55 (3H, s), 0.82 (3H, d), 0.84 (3H, d), 0.92 (3H, d), 1.01 (3H, d), 1.03 (6H, s), 1.71 (3H, s), 2.01 (3H, s), 2.35 (3H, s), 4.20 (1H, m), 5.01 (1H, s), 5.04 (1H, m), 5.22 (2H, m), 5.37 (1H, s), 5.74 (1H, s), 6.00-6.36 (6H, m), 7.01 (1H, m)

EXAMPLE 5

Preparation of 1α,25-dihydroxycholecalciferol Vitamin A Acid (All-trans Form) Ester (Compound I-5)

Compound VII-5 was prepared from Compound V via Compound VI-5 in the same procedures as in Example 3(1) and (2), except that triethylsilyl chloride was used instead of t-butyldimethylsilyl chloride in Example 3(1).

To a mixture of all-trans vitamin A acid (200 mg) and isopropyl ether (3 ml) was dropwise added trifluoroacetic anhydride (0.1 ml). and the mixture was stirred for 30 min. Then, a tetrahydrofuran solution (5 ml) of Compound VII-5 (270 mg) was added followed by stirring at room temperature for 2 hours. Addition of aqueous ammonia (0.5 ml), extraction with ether, washing with brine, subsequent removal of the ether by distillation and purification of the residue by chromatography on silica gel (hexane/ethyl acetate=95/5) afforded 330 mg of Compound VIII-5. To a solution of Compound VIII-5 (330 mg) in tetrahydrofuran (5 ml) was added a 1M solution of Bu₄NF (3 ml), and the mixture was stirred at 50° C. for 1 hour. Extraction with ethyl acetate, washing with brine, subsequent removal of the solvent and purification of the residue by chromatography on silica gel (hexane/ethyl acetate=4/1) yielded 190 mg of the title Compound I-5.

$^1$H-NMR (CDCl$_3$): δ0.54 (3H, s), 0.94 (3H, d), 1.03 (6H, s), 1.21 (6H, s), 1.71 (3H, s), 2.01 (3H, s), 2.35 (3H, s), 4.42 (1H, m), 5.00 (1H, s), 5.27 (1H, m), 5.35 (1H, s), 5.74 (1H, s), 6.00-6.37 (6H, m), 7.01 (1H, m)

EXAMPLE 6

Preparation of 1β,25-dihydroxycholecalciferol Vitamin A Acid (All-trans Form) Ester (Compound I-6)

Compound VII-6 was prepared from Compound V-6 via Compound VI-6 in the same procedures as in Example 5(1) and (2).

Compound VII-6 (200 mg) was treated in the same way as in Example 3(3) to give 90 mg of the title Compound I-6.

$^1$H-NMR (CDCl$_3$): δ0.53 (3H, s), 0.94 (3H, d), 1.03 (6H, s), 1.20 (6H, s), 1.71 (3H, s), 2.01 (3H, s), 2.35 (3H, s), 4.20 (1H, m), 5.00 (1H, s), 5.04 (1H, m), 5.36 (1H, s), 5.74 (1H, s), 6.00-6.36 (6H, m), 7.01 (1H, m)

EXAMPLE 7

Preparation of 1α25-dihydroxyergocalciferol Vitamin A Acid (All-trans Form) Ester (Compound I-7)

Compound VII-7 was prepared from Compound V-7 via Compound VI-7 in the same procedures as in Example 5(1) and (2).

Compound VII-7 (400 mg) was treated in the same way as in Example 3(3) to afford 290 mg of the title Compound I-7.

$^1$H-NMR (CDCl$_3$): δ0.54 (3H, s), 0.93 (3H, d), 1.00 (3H, d), 1.03 (6H, s), 1.16 (3H, s), 1.17 (3H, s), 1.71 (3H, s), 2.01 (3H, s), 2.35 (3H, s), 4.42 (1H, m), 5.00 (1H, s), 5.22 (2H, m), 5.27 (1H, m), 5.35 (1H, s), 5.74 (1H, s), 6.00-6.36 (6H, m), 7.02 (1H, m)

EXAMPLE 8

Preparation of 1β, 25-dihydroxyergocalciferol Vitamin A Acid (All-trans Form) Ester (Compound I-8)

Compound VII-8 was prepared from Compound V-8 via Compound VI-8 in the same procedures in Example 5(1) and (2).

Compound VII-8 (250 mg) was treated in the same way as in Example 3(3) to obtain 120 mg. of the title Compound I-8.

$^1$H-NMR (CDCl$_3$): δ0.53 (3H, s), 0.94 (3H, d), 1.01 (3H, d), 1.02 (6H, s), 1.15 (3H, s), 1.17 (3H, s), 1.70 (3H, s), 2.01 (3H, s), 2.34 (3H, s), 4.19 (1H, m), 5.01 (1H, s), 5.04 (1H, m), 5.23 (2H, m), 5.36 (1H, s), 5.75 (1H, s), 6.00-6.36 (6H, m), 7.00 (1H, m)

EXAMPLE 9

Preparation of 1α,24R-dihydroxycholecalciferol Vitamin A (All-trans Form) Ester (Compound I-9)

Compound VII-9 was prepared from Compound V-9 via Compound VI-9 in the same procedures as in Example 5(1) and (2).

Compound VII-9 (140 mg) was treated in the same way as in Example 3(3) to give 100 mg of the title Compound I-9.

$^1$H-NMR (CDCl$_3$): δ0.56 (3H, s), 0.96 (3H, d), 1.03 (6H, s), 1.17 (6H, d), 1.70 (3H, s), 2.01 (3H, s), 2.36 (3H, s), 3.22 (1H, m), 4.40 (1H, m), 4.97 (1H, s), 5.27 (1H, m), 5.33 (1H, s), 5.74 (1H, s), 6.00-6.38 (6H, m), 7.01 (1H, m)

EXAMPLE 10

Preparation of 1α,24S,25-trihydroxycholecalciferol Vitamin A (All-trans Form) Ester (Compound I-10)

Compound VII-10 was prepared from Compound V-10 via Compound VI-10 in the same procedures as in Example 5(1) and (2).

Compound VII-10 (80 mg) was treated in the same way as in Example 3(3) to afford the title Compound I-10 (35 mg).

$^1$H NMR (CD$_3$OD—CDCl$_3$): δ0.57 (3H, s), 0.97 (3H, d), 1.03 (6H, s), 1.21 (6H, d), 1.70 (3H, s), 2.01 (3H, s), 2.37 (3H, s), 3.25 (1H, m), 4.41 (1H, m), 4.97 (1H, s), 5.26 (1H, m), 5.33 (1H, s), 5.74 (1H, s), 6.01–6.39 (6H, m), 7.01 (1H, m)

EXAMPLE 11

Preparation of 1α-hydroxycholecalciferol Vitamin A Acid (13-cis Form) Ester (Compound I-11)

Compound VII-11 was prepared from Compound V-11 via Compound VI-11 in the same procedures as in Example 3(1) and (2).

Compound VII-11 (100 mg) was treated in the same way as in Example 3(3) except that the all-trans vitamin A acid used therein was replaced by 13-cis-vitamin A acid (100 mg) to give 95 mg of the title Compound I-11.

$^1$H-NMR (CDCl$_3$): δ0.54 (3H, s), 0.86 (3H, s), 0.87 (3H, s), 0.92 (3H, d), 1.03 (6H, s), 1.71 (3H, s), 2.03 (3H, s), 2.17 (3H, s), 4.43 (1H, m), 5.00 (1H, m), 5.30 (1H, m), 5.35 (1H, m), 5.95 (1H, s), 6.01–6.32 (5H, m), 7.04 (1H, d), 7.85 (1H, d)

EXAMPLE 12

Preparation of 1β-hydroxycholecalciferol Vitamin A Acid (13-cis Form) Ester (Compound I-12)

Compound VII-12 was prepared from Compound V-12 via Compound VI-12 in the same procedures as in Example 3(1) and (2).

Compound VII-12 (50 mg) was treated in the same way as in Example 3(3) except that the all-trans vitamin A acid used therein was replaced by 13-cis-vitamin A acid (60 mg) to obtain 30 mg of the title Compound I-12.

$^1$H-NMR (CDCl$_3$): δ0.54 (3H, s), 0.86 (3H, s), 0.87 (3H, s), 0.92 (3H, d), 1.03 (6H, s), 1.71 (3H, s), 2.03 (3H, s), 2.17 (3H, s), 4.20 (1H, m), 5.01 (1H, m), 5.05 (1H, m), 5.35 (1H, m), 5.95 (1H, s), 6.01–6.33 (5H, m), 7.04 (1H, d), 7.86 (1H, d)

EXAMPLE 13

Preparation of 1α-hydroxyergocalciferol Vitamin A Acid (13-cis Form) Ester (Compound I-13)

Compound VII-13 was prepared from Compound V-13 via Compound VI-13 in the same procedures as in Example 3(1) and (2).

Compound VII-13 (60 mg) was treated in the same way as in Example 3(3) except that the all-trans vitamin A acid used therein was replaced by 13-cis-vitamin A acid (50 mg) to give 30 mg of the title Compound I-13.

$^1$H-NMR (CDCl$_3$): δ0.55 (3H, s), 0.82 (3H, d), 0.84 (3H, d), 0.92 (3H, d), 1.01 (3H, d), 1.03 (3H, s), 1.71 (3H, s), 2.03 (3H, s), 2.17 (3H, s), 4.44 (1H, m), 5.01 (1H, m), 5.28 (1H, m), 5.34 (1H, m), 5.20 (2H, m), 5.95 (1H, s), 6.00–6.35 (5H, m), 7.04 (1H, d), 7.84 (1H, d)

EXAMPLE 14

Preparation of 1β-hydroxyergocalciferol Vitamin A Acid (13-cis Form) Ester (Compound I-14)

Compound VII-14 was prepared from Compound V-14 via Compound VI-14 in the same procedures as in Example 3(1) and (2).

Compound VII-14 (60 mg) was treated in the same way as in Example 3(3) except that the all-trans vitamin A acid used therein was replaced by 13-cis-vitamin A acid (50 mg) to give 25 mg of the title Compound I-14.

$^1$H-NMR (CDCl$_3$): δ0.55 (3H, s), 0.82 (3H, d), 0.84 (3H, d), 0.92 (3H, d), 1.01 (3H, d), 1.03 (6H, s), 2.03 (3H, s), 2.17 (3H, s), 4.21 (1H, m), 5.00 (1H, m), 5.04 (1H, m), 5.22 (2H, m), 5.36 (1H, m), 5.95 (1H, s), 6.01–6.35 (5H, m), 7.05 (1H, d), 7.87 (1H, d)

EXAMPLE 15

Preparation of 1α,25-dihydroxycholecalciferol Vitamin A Acid (13-cis Form) Ester (Compound I-15)

Compound VII-15 was prepared from Compound V-15 via Compound VI-15 in the same procedures as in Example 5(1) and (2).

Compound VII-15 (60 mg) was treated in the same way as in Example 3(3) except that the all-trans vitamin A acid used therein was replaced by 13-cis-vitamin A acid (50 mg) to give 40 mg of the title Compound I-15.

$^1$H-NMR (CDCl$_3$): δ0.54 (3H, s), 0.94 (3H, d), 1.03 (6H, s), 1.21 (6H, s), 1.71 (3H, s), 2.01 (3H, s), 2.35 (3H, s), 4.42 (1H, m), 5.00 (1H, s), 5.27 (1H, m), 5.35 (1H, s), 5.94 (1H, s), 6.01–6.35 (5H, m), 7.05 (1H, d), 7.86 (1H, d)

EXAMPLE 16

Preparation of 1β,25-dihydroxycholecalciferol Vitamin A Acid (13-cis Form) Ester (Compound I-16)

Compound VII-16 was prepared from Compound V-16 via Compound VI-16 in the same procedures as in Example 5(1) and (2).

Compound VII-16 (60 mg) was treated in the same way as in Example 3(3) except that the all-trans vitamin A acid used therein was replaced by 13-cis-vitamin A acid (50 mg) to give 25 mg of the title Compound I-16.

$^1$H-NMR (CDCl$_3$): δ0.53 (3H, s), 0.94 (3H, d), 1.03 (6H, s), 1.20 (6H, s), 1.71 (3H, s), 2.01 (3H, s), 2.35 (3H, s), 4.21 (1H, m), 5.00 (1H, s), 5.04 (1H, m), 5.36 (1H, s), 5.95 (1H, s), 6.01–6.34 (5H, m), 7.04 (1H, d), 7.87 (1H, d)

EXAMPLE 17

Preparation of 1α,25-dihydroxyergocalciferol Vitamin A Acid (13-cis Form) Ester (Compound I-17)

Compound VII-17 was prepared from Compound V-17 via Compound VI-17 in the same procedures as in Example 5(1) and (2).

Compound VII-17 (60 mg) was treated in the same way as in Example 3(3) except that the all-trans vitamin A acid used therein was replaced by 13-cis-vitamin A acid (50 mg) to afford 45 mg of the title Compound I-17.

$^1$H-NMR (CDCl$_3$): δ0.54 (3H, s), 0.93 (3H, d), 1.00 (3H, d), 1.03 (6H, s), 1.16 (3H, s), 1.17 (3H, s), 1.71 (3H, s), 2.01 (3H, s), 2.35 (3H, s), 4.42 (1H, m), 5.00 (1H, s), 5.23 (2H, m), 5.27 (1H, m), 5.35 (1H, s), 5.95 (1H, s), 6.01–6.34 (5H, m), 7.05 (1H, d), 7.86 (1H, d)

EXAMPLE 18

Preparation of 1β,25-dihydroxyergocalciferol Vitamin A (13-cis Form) Ester (Compound I-18)

Compound VII-18 was prepared from Compound V-18 via Compound VI-18 in the same procedures as in Example 5(1) and (2).

Compound VII-18 (60 mg) was treated in the same way as in Example 3(3) except that the all-trans vitamin A acid used therein was replaced by 13-cis-vitamin A acid (50 mg) to afford 30 mg of the title Compound I-18.

$^1$H-NMR (CDCl$_3$): δ0.53 (3H, s), 0.94 (3H, d), 1.00 (3H, d), 1.02 (6H, s), 1.16 (3H, s), 1.17 (3H, s), 1.70 (3H, s), 2.01 (3H, s), 2.34 (3H, s), 4.19 (1H, m), 5.01 (1H, s), 5.04 (1H, m), 5.23 (2H, m), 5.36 (1H, s), 5.95 (1H, s), 6.00–6.34 (5H, m), 7.04 (1H, d), 7.87 (1H, d)

What is claimed is:

1. A 1-hydroxyvitamin D derivative having the formula (I)

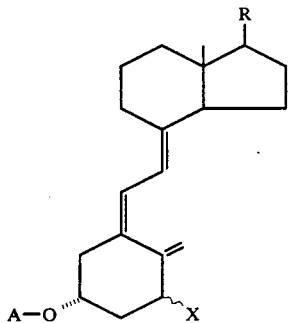
(I)

wherein A represents an acyl residue derived from vitamin A acid, X means a hydroxyl group and R represents a group of the formula (II)

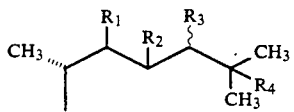
(II)

wherein $R_1$ and $R_2$ each represent hydrogen atoms or together form a carbon-carbon double bond, $R_3$ represents a hydrogen atom, a $C_1$–$C_4$ alkyl group or a hydroxyl group and $R_4$ represents a hydrogen atom or a hydroxyl group.

2. The compound according to claim 1 wherein A is an acyl group derived from all-trans vitamin A having the formula (III)

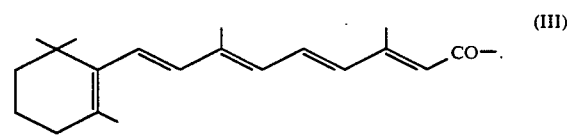
(III)

3. The compound according to claim 1 wherein A is an acyl group derived from 13-cis-vitamin A having the formula (IV)

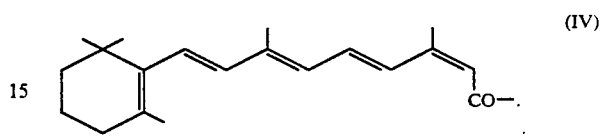
(IV)

4. The compound according to claim 2 wherein $R_1$ and $R_2$ each represent hydrogen atoms, $R_3$ represents a hydrogen atom, a $C_1$–$C_4$ alkyl group or a hydroxyl group and $R_4$ represents a hydrogen atom or a hydroxyl group.

5. The compound according to claim 2 wherein $R_1$ and $R_2$ together form a carbon-carbon double bond, $R_3$ represents a hydrogen atom, a $C_1$–$C_4$ alkyl group or a hydroxyl group and $R_4$ represents a hydrogen atom or a hydroxyl group.

6. The compound according to claim 3 wherein $R_1$ and $R_2$ each represent hydrogen atoms, $R_3$ represents a hydrogen atom, a $C_1$–$C_4$ alkyl group or a hydroxyl group and $R_4$ represents a hydrogen atom or a hydroxyl group.

7. The compound according to claim 3 wherein $R_1$ and $R_2$ together form a carbon-carbon double bond, $R_3$ represents a hydrogen atom, a $C_1$–$C_4$ alkyl group or a hydroxyl group and $R_4$ represents a hydrogen atom or a hydroxyl group.

* * * * *

UNITED STATES PATENT AND TRADEMARK OFFICE
CERTIFICATE OF CORRECTION

PATENT NO. : 5,182,396

DATED : January 26, 1993

INVENTOR(S) : TACHIBANA

It is certified that error appears in the above-identified patent and that said Letters Patent is hereby corrected as shown below:

At column 13, line 14, delete "VII-11", insert -- VII-1 --.

At column 13, line 15, delete "V-11", insert -- V-1 --.

At column 13, line 15, delete "VI-11", insert -- VI-1 --.

At column 13, line 17, delete "VII-11", insert -- VII-1 --.

Col. 13, line 31, delete "VII-12" insert --VII-2--

At column 13, line 32, delete "V-12", insert -- V-2 --.

At column 13, line 32, delete "VI-12", insert -- VI-2 --.

At column 13, line 34, delete "VII-12", insert -- VII-2 --.

At column 13, line47, delete "VII-13", insert -- VII-3 --.

At column 13, line 48, delete "V-13", insert -- V-3 --.

UNITED STATES PATENT AND TRADEMARK OFFICE
CERTIFICATE OF CORRECTION

PATENT NO. : 5,182,396
DATED : January 26, 1993
INVENTOR(S) : TACHIBANA

It is certified that error appears in the above-identified patent and that said Letters Patent is hereby corrected as shown below:

At column 13, line 48, delete "VI-13", insert -- VI-3 --.

At column 13, line 50, delete "VII-13", insert -- VII-3 --.

At column 13, line 64, delete "VII-14", insert -- VII-4 --.

Column 13, line 65, delete "V-14" insert --V-4--

At column 13, line 65, delete "VI-14", insert -- VI-4 --.

At column 13, line 67, delete "VII-14", insert -- VII-4 --.

At column 14, line 13, delete "VII-15", insert -- VII-5 --.

At column 14, line 14, delete "V-15", insert -- V-5 --.

At column 14, line 14, delete "VI-15", insert -- VI-5 --.

At column 14, line 16, delete "VII-15", insert -- VII-5 --.

UNITED STATES PATENT AND TRADEMARK OFFICE
CERTIFICATE OF CORRECTION

PATENT NO. : 5,182,396
DATED : January 26, 1993
INVENTOR(S) : TACHIBANA

It is certified that error appears in the above-identified patent and that said Letters Patent is hereby corrected as shown below:

At column 14, line 28, delete "VII-16" insert -- VII-6 --.

At column 14, line 29, delete "V-16" insert -- V-6 --.

At column 14, line 29, delete "VI-16", insert -- VI-6 --.

At column 14, line 31, delete "VII-16" insert -- VII-6 --.

At column 14, line 43, delete "VII-17", insert -- VII-7 --.

At column 14, line 44, delete "V-17", insert -- V-7 --.

At column 14, line 44, delete "VI-17", insert -- VI-7 --.

At column 14, line 46, delete "VII-17", insert -- VII-7 --.

At column 14, line 60, delete "VII-18", insert -- VII-8 --.

At column 14, line 61, delete "V-18", insert -- V-8 --.

At column 14, line 61, delete "VI-18", insert -- VI-8 --.

UNITED STATES PATENT AND TRADEMARK OFFICE
CERTIFICATE OF CORRECTION

PATENT NO. : 5,182,396
DATED     : January 26, 1993
INVENTOR(S) : Tachibana

It is certified that error appears in the above-indentified patent and that said Letters Patent is hereby corrected as shown below:

Column 14, line 63, delete "VII-18", insert --VII-8--

Signed and Sealed this

Twenty-second Day of March, 1994

Attest:

BRUCE LEHMAN

*Attesting Officer*     *Commissioner of Patents and Trademarks*